United States Patent
Hjelt et al.

(10) Patent No.: US 7,103,407 B2
(45) Date of Patent: Sep. 5, 2006

(54) BODY FAT MONITORING SYSTEM AND METHOD EMPLOYING MOBILE TERMINAL

(75) Inventors: Kari Hjelt, Espoo (FI); Kjell Nybergh, Sipoo (FI); Jari Hyyryläinen, Veikkola (FI); Tapani Ryhänen, Helsinki (FI); Santtu Naukkarinen, Espoo (FI)

(73) Assignee: Nokia Corporation, Espoo (FI)

( * ) Notice: Subject to any disclaimer, the term of this patent is extended or adjusted under 35 U.S.C. 154(b) by 430 days.

(21) Appl. No.: 10/186,246

(22) Filed: Jun. 28, 2002

(65) Prior Publication Data

US 2004/0002662 A1    Jan. 1, 2004

(51) Int. Cl.
*A61B 5/05* (2006.01)

(52) U.S. Cl. .................................. 600/547

(58) Field of Classification Search ............. 600/547, 600/548, 300
See application file for complete search history.

(56) References Cited

U.S. PATENT DOCUMENTS

| | | | |
|---|---|---|---|
| 5,372,141 A * | 12/1994 | Gallup et al. | 600/547 |
| D399,153 S | 10/1998 | Yamauchi et al. | |
| 5,817,031 A | 10/1998 | Masuo et al. | |
| D419,089 S | 1/2000 | Yamauchi et al. | |
| 6,243,651 B1 | 6/2001 | Masuo | |
| 6,308,096 B1 | 10/2001 | Masuo | |
| 6,321,112 B1 | 11/2001 | Masuo | |
| 6,327,495 B1 * | 12/2001 | Iwabuchi et al. | 600/547 |
| 6,456,873 B1 * | 9/2002 | Inoue et al. | 600/547 |
| D467,192 S | 12/2002 | Itagaki et al. | |
| 6,694,182 B1 * | 2/2004 | Yamazaki et al. | 600/547 |
| 6,790,178 B1 * | 9/2004 | Mault et al. | 600/300 |
| 2002/0019586 A1 | 2/2002 | Teller et al. | |

FOREIGN PATENT DOCUMENTS

| | | |
|---|---|---|
| EP | 1 027 860 A1 | 8/2000 |
| EP | 1 138 259 A2 | 10/2001 |
| EP | 1 193 494 A1 | 4/2002 |
| EP | 1 211 870 | 6/2002 |
| JP | 11202087 | 12/2000 |
| JP | 2000016993 | 8/2001 |
| JP | 2001-346783 | 12/2001 |
| JP | 2000174638 | 12/2001 |
| JP | 2000174639 | 12/2001 |
| WO | WO 01/80437 | 10/2001 |

OTHER PUBLICATIONS

Harvey Weinberg, *Using the ADXL 202 in Pedometer and Personal Navigation Applications*, Technical Note, One Technology Way, P.O. Box 9106. Norwood, Massachusetts 02062-9106. http://www.analog.com/techsupt/application.

* cited by examiner

*Primary Examiner*—Eric F. Winakur
(74) *Attorney, Agent, or Firm*—Hollingsworth & Funk, LLC

(57) ABSTRACT

A system and method measures a parameter of body fat using body fat monitoring circuitry provided with a mobile communications device or device cover. A mobile terminal device includes a housing supporting a display, a processor, and a user interface for facilitating user interaction with the mobile terminal device. Body fat monitoring circuitry of the mobile terminal device includes a tactile interface supported by one or both of the housing and a cover of the housing. The monitoring circuitry communicates monitoring signals to a portion of a user's body via the tactile interface. The processor computes a resistance to the communication of the monitoring signals and computes the user's body fat parameter using the computed resistance. An acceleration sensor may be included to provide various pedometer functions.

51 Claims, 9 Drawing Sheets

BODY FAT MONITORING SYSTEM AND METHOD EMPLOYING MOBILE TERMINAL

FIELD OF THE INVENTION

The present invention relates generally to communication of user information via a mobile terminal and, more particularly, to systems and methods for measuring physiological conditions of a user via monitoring circuitry provided in a mobile terminal or a cover of a mobile terminal.

BACKGROUND OF THE INVENTION

Weight management through reduction of excess body fat plays a vital role in maintaining good health and fighting disease. Medical evidence has shown that excess body fat poses a major threat to health and longevity. Excess body fat is linked to major physical threats, such as heart disease, cancer, and diabetes. A certain amount of fat, however, is essential to bodily functions. Fat regulates body temperature, cushions and insulates organs and tissues, and is the main form of the body's energy storage.

Weight alone is not a clear indicator of good health, because it does not distinguish between pounds that come from body fat and those that come from lean body mass or muscle. Various body fat measuring devices have been developed to better quantify the amount of body fat as a percentage of total body mass. Although many of these devices provide accurate body fat measurements, such devices tend to be expensive and offer limited functionality beyond a basic measuring capability.

As contemporary lifestyles have become increasingly fast-paced and complicated, the number of personal electronic devices carried on the person has increased. It is not uncommon for an individual to carry a cellular phone, a PDA, some form of calculator, a pager, and a portable personal medical device, such as a body fat measuring device, heart rate monitor or pedometer, for example. The inconvenience of physically transporting and accounting for such devices often results in eliminating certain devices from one's personal inventory of devices. In many cases, personal medical devices, such as body fat monitoring devices, which can enhance exercise regimens and provide motivation for healthier lifestyle habits, are cast aside in favor of more utilitarian devices, such as the now ubiquitous cellular phone.

There is a need for integration of mobile communications and health promoting devices, such as body fat monitoring devices. The present invention addresses this and other needs, and provides additional features and advantages over conventional implementations and techniques.

SUMMARY OF THE INVENTION

The present invention is directed to a system and method for measuring a parameter of body fat using body fat monitoring circuitry embodied in a portable device or structure. In one embodiment, body fat monitoring circuitry is provided with a mobile communications device, such as a mobile terminal. In another embodiment, body fat monitoring circuitry is incorporated as part of a portable cover, such as a cover for a mobile terminal or other portable electronic or communications device. Other physiological parameters can also be measured, such as parameters associated with fat mass, total body water, dehydration, body fluid, and body fluid balance, for example.

According to one embodiment, a mobile terminal device of the present invention includes a housing supporting a display, a processor, and a user interface for facilitating user interaction with the mobile terminal device. The mobile terminal device further includes body fat monitoring circuitry comprising a tactile interface supported by one or both of the housing and a cover of the housing. The monitoring circuitry communicates monitoring signals to a portion of a user's body via the tactile interface. The monitoring signals produced by the monitoring circuitry are typically sinusoidal current or voltage signals or square wave current or voltage signals.

The processor computes a parameter associated with the user's body fat in response to the communication of the monitoring signals into the user's body tissue. In particular, the processor computes a resistance to the communication of the monitoring signals and computes the user's body fat parameter using the computed resistance.

The tactile interface includes a number of electrodes, such as four electrodes, supported by one or both of the housing and housing cover. In one arrangement, the electrodes are supported by a common surface, such as the cover of the housing. In another arrangement, the electrodes are supported by two or more surfaces of the housing and/or housing cover.

According to a further arrangement, the user interface of the mobile terminal device includes a keypad, and some or all of the electrodes are integrated into one or more keys of the keypad. The mobile terminal device is preferably capable of over-the-air (OTA) communication with a network, and can further include circuitry for accessing one or more network services associated with user fitness or health.

In accordance with another embodiment, a mobile terminal device of the type described above further includes an acceleration sensor. A processor, according to this embodiment, computes a parameter associated with the user's body fat in response to the communication of body fat monitoring signals into the body and uses an acceleration signal produced by the acceleration sensor to compute a parameter associated with walking or running by the user.

The acceleration signal can constitute a counter signal indicative of a number of steps taken by the user. The parameter associated with walking or running by the user can include a distance traveled by the user, calories consumed by the user during walking or running, average speed or average steps per minute.

According to a further embodiment, a method of using a mobile terminal device for facilitating wireless communication and body fat monitoring involves providing a mobile terminal device having body fat monitoring circuitry. The body fat monitoring circuitry includes a number of electrodes for contacting portions of a user's hands. Monitoring signals are transmitted between a first pair of the electrodes when in contact with the user's hands. A resistance is detected between a second pair of the electrodes in response to transmission of the monitoring signals. A parameter associated with the user's body fat is computed using the detected resistance.

In one measuring arrangement, the first pair of electrodes are situated on the mobile terminal device to contact a distal portion of a palm of each of the user's hands, and the second pair of electrodes are situated on the mobile terminal device to contact a proximal portion of the palm of each of the user's hands. In another measuring arrangement, the first pair of electrodes are situated on the mobile terminal device to contact an index finger of each of the user's hands, and the second pair of electrodes are situated on the mobile terminal device to contact a thumb of each of the user's hands. In a further measuring arrangement, the first pair of electrodes are situated on the mobile terminal device to contact a middle finger of each of the user's hands, and the second pair of electrodes are situated on the mobile terminal device to contact an index finger of each of the user's hands.

In accordance with another embodiment, the mobile terminal device further includes an acceleration sensor, and the body fat monitoring method further involves computing a parameter associated with walking or running by the user by use of an acceleration signal produced by the acceleration sensor.

The body fat parameter can constitute percent body fat, and the method can further involve wirelessly communicating the percent body fat of the user and the parameter associated with walking or running to a remote data system. The method can further involve receiving a message concerning one or both of the user's percent body fat and a recommended walking or running regimen from the remote data system. The method can also involve communicating with a network and accessing one or more mobile network services associated with user fitness or health. In another embodiment, electrical signals can be communicated between the mobile terminal device and a device external to the mobile terminal device via an electrical conductor coupled between at least some of the electrodes and the external device.

According to yet another embodiment, a portable cover of the present invention includes a processor and physiological conditions monitoring circuitry. An interface couples the processor with the monitoring circuitry. The physiological conditions monitoring circuitry includes a tactile interface supported by one or more surfaces of the cover. The monitoring circuitry communicates monitoring signals to a portion of a user's body via the tactile interface. The processor computes a parameter associated with a user's physiological conditions in response to communication of the monitoring signals.

The parameter computed by the processor is preferably associated with the user's body fat. The tactile interface typically includes a plurality of electrodes. The monitoring circuitry can further include one or more accelerometers. A device interface is preferably configured to communicatively couple the processor of the portable cover with a mobile communications device.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
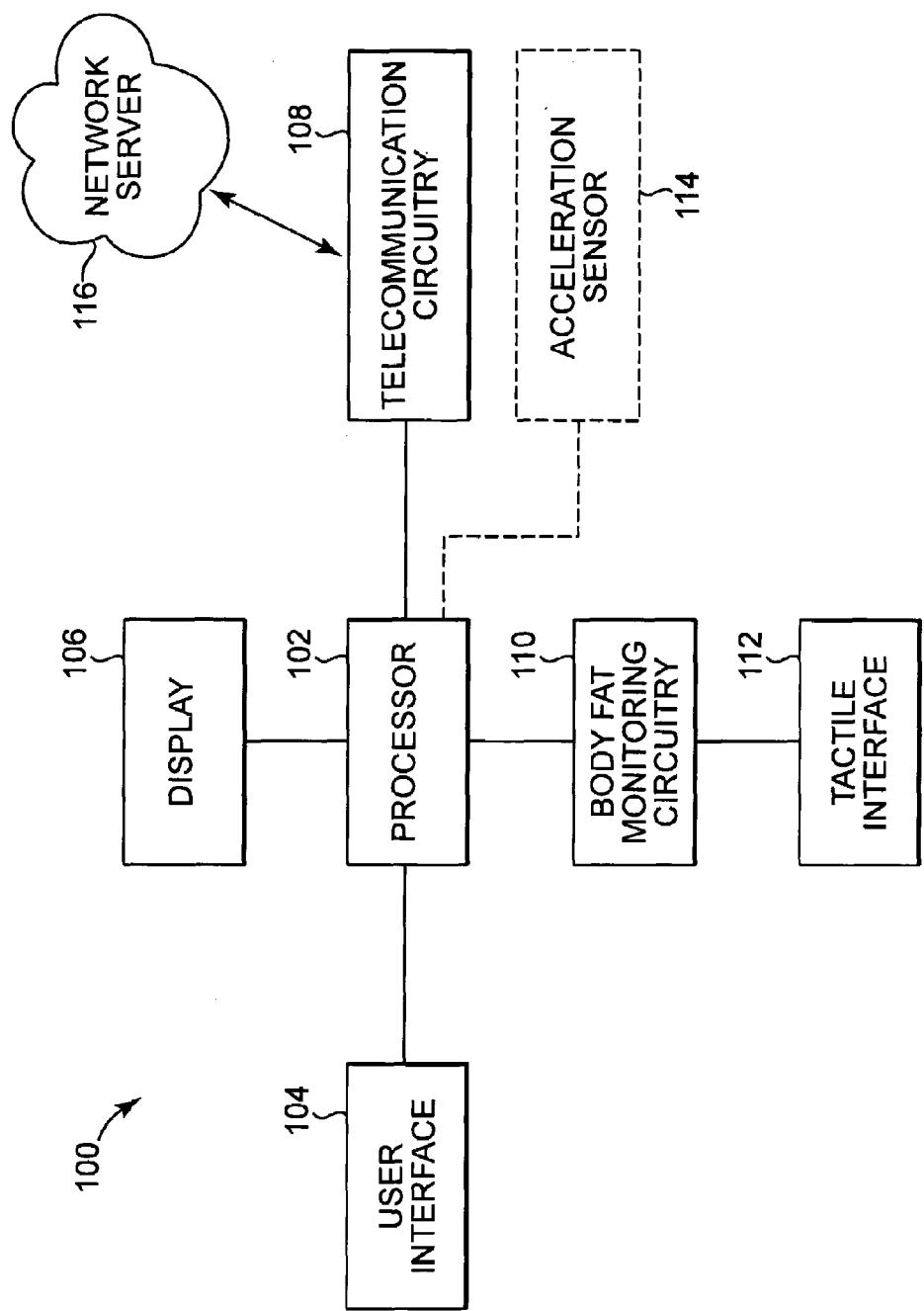
FIG. 1 illustrates a system for measuring one or more body fat parameters incorporated as part of a mobile communications device, such as a mobile terminal, in accordance with an embodiment of the present invention.

While the invention is amenable to various modifications and alternative forms, specifics thereof have been shown by way of example in the drawings and will be described in detail. It is to be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF VARIOUS EMBODIMENTS

In the following description of the illustrated embodiments, reference is made to the accompanying drawings which form a part hereof, and in which is shown by way of illustration, various embodiments in which the invention may be practiced. It is to be understood that the embodiments may be utilized and structural changes may be made without departing from the scope of the present invention.

The present invention is directed to systems and methods that provide for mobile communication capabilities and measurement of one or more body fat parameters. According to an embodiment of the present invention, a mobile communications device, such as a mobile terminal or node, incorporates body fat monitoring circuitry that allows for easy, convenient non-invasive measuring of one or more body fat parameters, such as percent body fat, for example.

Incorporating body fat monitoring circuitry within a mobile terminal allows for increased body fat measuring capabilities, and reduced cost, when compared to stand-alone body fat measuring systems, owing to the exploitation of the processing, memory, user interface, and display capabilities already built into the mobile terminal.

Further, the inherent mobile communication capabilities of the mobile terminal provide for enhanced functionality, such as storage of body fat parameters and related data in a user accessible fitness profile on a network server, which can be accomplished in real-time. Fitness recommendations and associated health information developed in response to the user's stored body fat parameters can be communicated from the network server to the user via the mobile terminal or other network access device, such as a WEB terminal device. By way of example, selected exercise regimens and diet options can be communicated to the user in response to body fat information transmitted from the mobile terminal to the network server. Other enhanced capabilities are realizable by combining the fat monitoring and mobile communication capabilities in accordance with the present invention.

Turning now to FIG. 1, there is illustrated a system 100 for measuring one or more body fat parameters incorporated as part of a mobile communications device, such as a mobile terminal, in accordance with an embodiment of the present invention. The system 100 utilizes existing components of the mobile terminal in combination with body fat monitoring circuitry 110. In certain configurations in which pedometer functionality is provided, the system 100 includes an acceleration sensor 114 which is coupled to the processor 102. The acceleration sensor 114 can alternatively be incorporated as part of the body fat monitoring circuitry 110.

A processor 102 of the mobile terminal is coupled to the body fat monitoring circuitry 110. A user interface 104 is coupled to the processor 102 which permits user interaction with the mobile terminal in a conventional manner. Also coupled to the processor 102 is a display 106 and telecommunications circuitry 108. The telecommunications circuitry 108 provides for communication between the mobile terminal and a radio network 116, such as a 2G or 3G network. It is noted that the network 116 can be representative of an IP or Mobil IP network, such as an IPv4, IPv6, or hybrid IPv4/IPv6 network for example.

As is further shown in FIG. 1, the body fat monitoring circuitry 110 is coupled to a tactile interface 112. The tactile interface 112 can be implemented in a variety of configurations for contacting the user's body in order to perform body fat monitoring. The tactile interface 112 can include, for example, a number of electrodes which provide for physical and electrical coupling between portions of the user's anatomy and the body fat monitoring circuitry 110 of the mobile terminal. In other configurations, optical sensing devices (e.g., optical pulse oximeters, optical or photonic blood chemistry sensors), blood pressure sensors, and body temperature sensors, for example, may be incorporated into the tactile interface 112, exclusive of, or in addition to, an array of electrodes.

In accordance with the non-limiting embodiments described in the instant disclosure, the tactile interface 112 will be described as including a number of source and detection electrodes which provide for electrical connectivity between the user and the mobile terminal when performing body fat measurements. It is understood that the tactile interface 112 can be implemented using other components, technologies, and physiological sensing methodologies, and that physiological parameters in addition to body fat parameters can be acquired by the tactile interface 112.

Figure 2A:
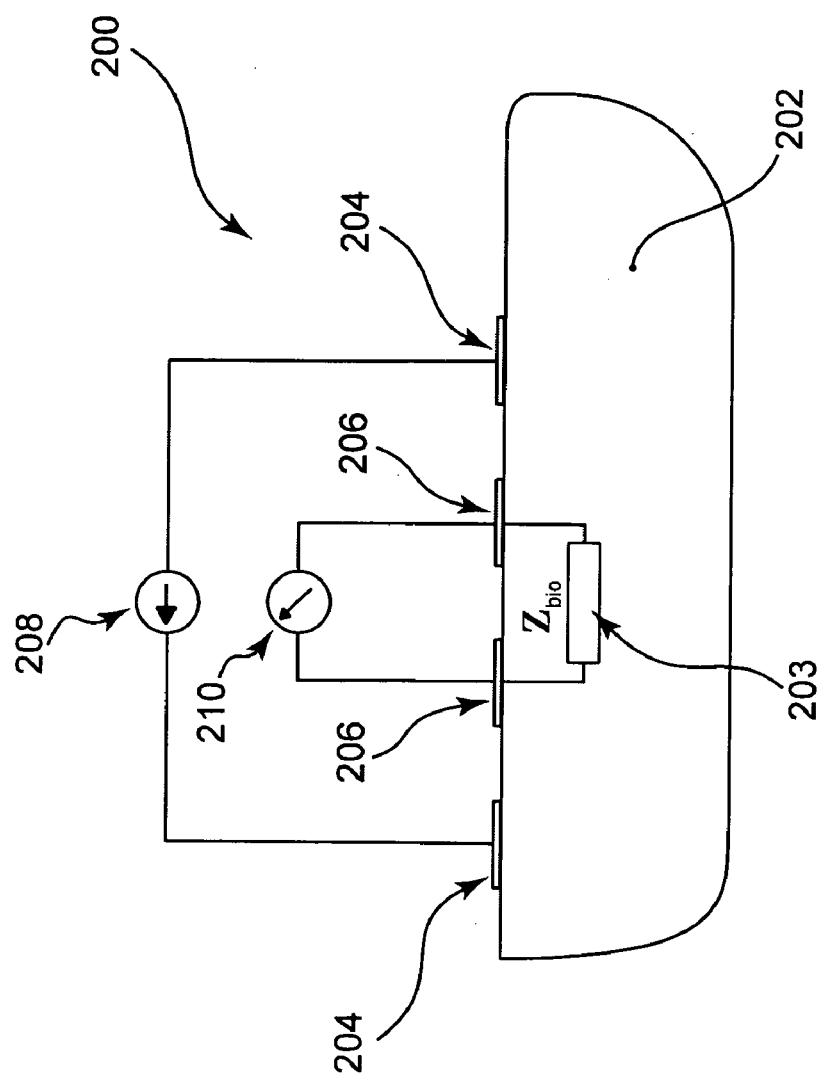
FIG. 2A illustrates body fat monitoring circuitry of a mobile communications device implemented to perform body fat percentage measurements using a four point probe technique in accordance with an embodiment of the present invention.

Referring now to FIG. 2A, there is illustrated body fat monitoring circuitry of a mobile communications device implemented to perform body fat percentage measurements using a four point probe technique in accordance with an embodiment of the present invention. The body fat monitoring circuitry 200 of FIG. 2A is depicted as being in physical contact with a portion 202 of a user's anatomy. According to a four point probe technique, two electrodes 204 serve as source electrodes and two electrodes 206 serve as detection electrodes. In general terms, body fat is determined by measuring the resistance 203 of the body to an injected monitoring signal using a four point probe technique.

The body fat monitoring circuitry 200 includes a monitoring signal generator 208, which is typically a current or voltage source that provides a constant current or voltage monitoring signal. The monitor signal generator 208 is coupled to the two source electrodes 204. It can be appreciated that the battery of the mobile terminal provides the requisite power to the body fat monitoring circuitry 200. The body fat monitoring circuitry 200 further includes a voltage detector 210 which is coupled between the two detection electrodes 206. The voltage detector 210 typically receives an input reference signal from the monitoring signal generator 208.

The monitoring signal generator 208 preferably generates an AC drive current signal. The drive current signal can be a sinusoidal signal or a square wave. The frequency of the drive current signal is preferably about 50 kHz or greater. It is noted that the frequency of the drive current signal can be varied and that body fat measurements can be made at each of a number of different frequencies. The drive current signal preferably has an amperage less than about 1 mA, and more preferably between about 0.3 mA and about 0.8 mA.

In normal operation, a monitoring signal generated by the monitoring signal generator 208 is injected into the user's body via the source electrodes 204. A current field is produced between the source electrodes 204 in response to propagation of the monitoring signal into the user's body tissue. The detection electrodes 206 are situated such that the current field is detectable. A sense voltage is developed between the detection electrodes 206 and measured by the voltage detector 210.

An impedance, $Z_{bio}$, is derivable using the sense voltage and source current amperage. The derived impedance value is reflective of a biological resistance and reactance (i.e., bioimpedance, $Z_{bio}$) measurable between the detection electrodes 206 in response to the monitoring signals injected into biological tissue by the source electrodes 204. Resistance accounts for more than 95% of the biological impedance value. As such, the biological resistance component of the bioimpedance is preferably used to derive body fat parameters, which results in a simplified design with very good accuracy. In general, a larger detected resistance 203 is indicative of a greater amount of body fat.

Figure 2B:
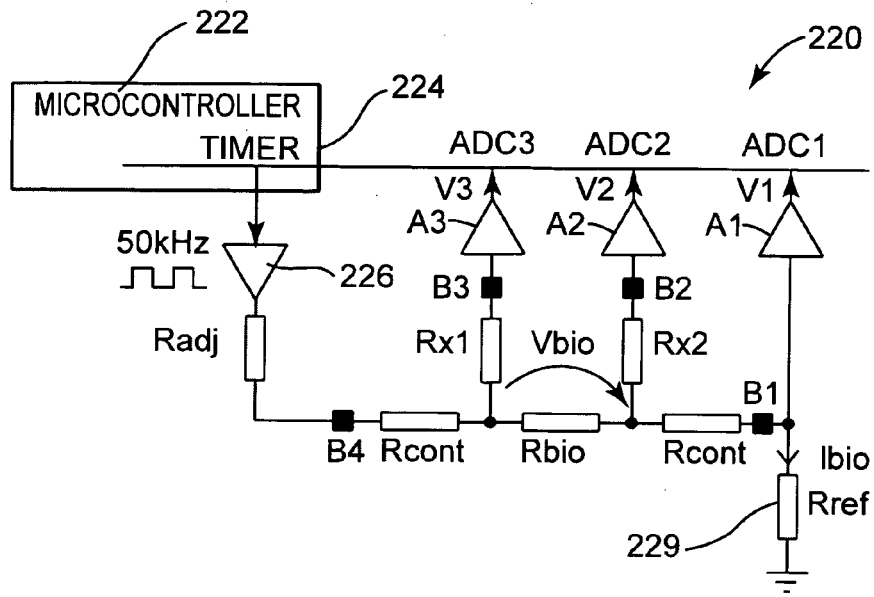
FIG. 2B is a schematic of body fat monitoring circuitry which employs square wave monitoring signals in accordance with an embodiment of the present invention.

FIG. 2B is a schematic of body fat monitoring circuitry which employs square wave monitoring signals in accordance with an embodiment of the present invention. In FIG. 2B, elements B1, B2, B3, and B4 represent electrodes (B1 and B4 are source electrodes, B2 and B3 are detection electrodes in this configuration), $R_{cont}$ represents contact resistance, $R_{x1}$ and $R_{x2}$ represent bioresistances in the hand, and $R_{bio}$ represents the bioresistance that is measured and indicative of body fat.

According to this embodiment, a timer 224, under control of a microcontroller 222, generates a square wave drive signal, which is connected to the source or drive electrode B4 via a buffer amplifier 226 and resistor $R_{adj}$. Timer 224 generates a square wave drive signal ($I_{bio}$) having a frequency of about 50 kHz or greater. Resistor $R_{adj}$ can be used to set the amperage ranging between about 0.4 mA and about 0.8 mA. The square wave generator is preferably configured as a constant current source.

Voltages $V_3$, $V_2$, and $V_1$ represent voltages developed at the respective outputs of instrument amplifiers A3, A2, and A1 in response to injection of the monitoring signal into the user's hands. Voltages $V_3$, $V_2$, and $V_1$ are input to respective analog-to-digital converters ADC3, ADC2, and ADC1. The respective digital voltage signals corresponding to analog voltages $V_3$, $V_2$, and $V_1$ are input to the microcontroller 222. The microcontroller 222, or the processor of the mobile terminal, can compute the bioresistance, $R_{bio}$, using the following equation:

$$R_{bio} = \frac{V_{bio}}{I_{bio}} = R_{ref} \cdot \frac{V_3 - V_2}{V_1} \quad [1]$$

where, $V_{bio}$ represents the voltage drop between detection electrodes B3 and B2, $R_{ref}$ represents the reference resistance, and $I_{bio}$ represents the drive current passing through the body from the hands via the source electrodes B4 and B1. The value of $I_{bio}$ can be determined by measuring the voltage across the resistor $R_{ref}$. It can be seen from Equation [1] above that employment of a four point probe technique advantageously eliminates the contact resistance, $R_{cont}$, from the body fat measurement. It is noted that various circuit components shown in FIG. 2B can be integrated as part of the microcontroller 222, such as the timer 224, amplifier 226, instrument amplifiers A1–A3, and A/D converters ADC1–ADC3.

Figure 2C:
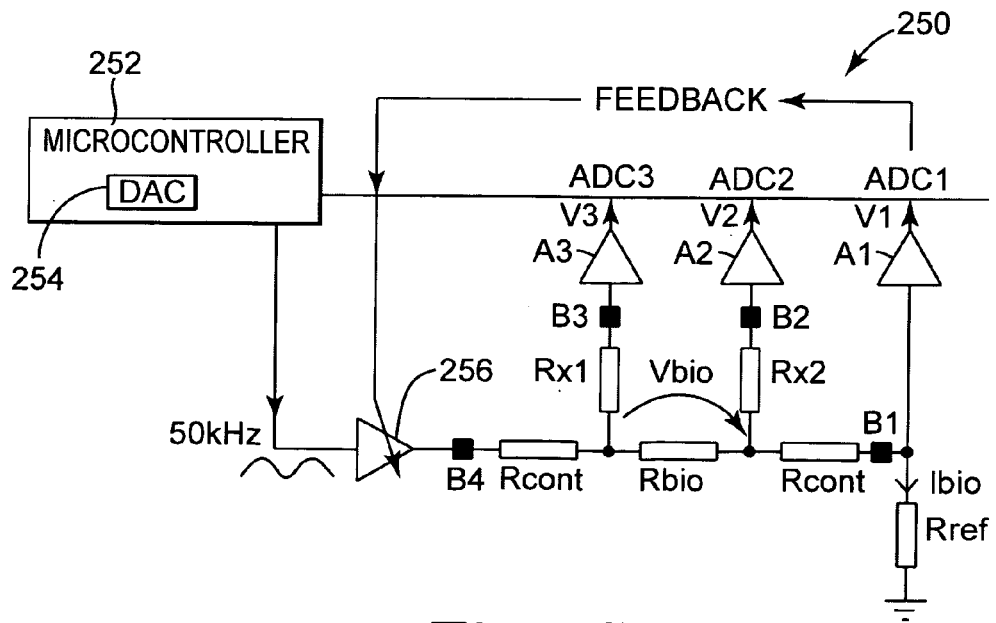
FIG. 2C is a schematic of body fat monitoring circuitry which employs sinusoidal monitoring signals in accordance with an embodiment of the present invention.

FIG. 2C is a schematic of body fat monitoring circuitry, which employs sinusoidal monitoring signals in accordance with another embodiment of the present invention. According to this implementation, a sinusoidal drive signal is generated at the output of a digital-to-analog converter (DAC) 254 under control of a microcontroller 252. The drive current signal, $I_{bio}$, preferably has a frequency of at least 50 kHz and an amperage ranging between about 0.4 mA and about 0.8 mA.

The drive current signal produced at the output of DAC 254 is applied to an input of an instrument amplifier 256. Feedback is added to insure that the drive current, $I_{bio}$, is kept substantially constant at a predetermined amperage, such as at about 0.6 mA. The circuitry shown in FIG. 2C operates in the manner described above with regard to the circuitry of FIG. 2B in response to the application of a sinusoidal drive current, $I_{bio}$. The bioresistance, $R_{bio}$, can be computed using Equation [1] above.

Figure 2D:
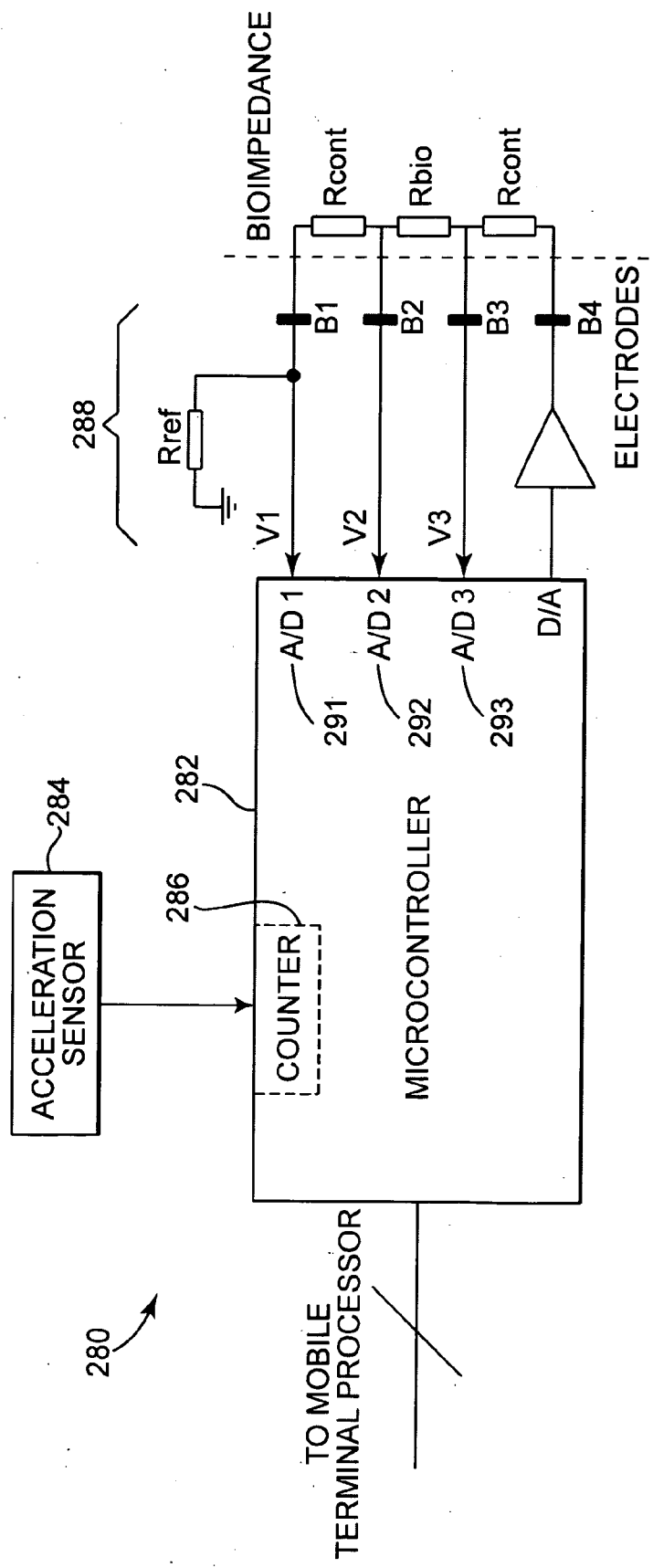
FIG. 2D is a schematic of body fat monitoring circuitry which employs an acceleration sensor to provide for a number of pedometer functions in accordance with an embodiment of the present invention.

FIG. 2D is a schematic of body fat monitoring circuitry which employs an acceleration sensor to provide for a number of pedometer functions in accordance with an embodiment of the present invention. According to this embodiment, the body fat measuring circuitry 288 can be implemented in accordance with the circuitry of FIGS. 2B and 2C. A microcontroller 282 includes at least three A/D converter ports 291, 292, 293, to which voltages V1, V2, V3 are respectively applied. The value of $R_{bio}$ can be computed by microcontroller 282 in a manner described previously.

In addition to providing a body fat measuring capability, the embodiment shown in FIG. 2D includes an acceleration sensor 284 which is coupled to the microcontroller 282. An output of the acceleration sensor 284 is preferably coupled to a counter 286, which is primarily employed to count steps taken by the user during walking or running. Inclusion of one or more acceleration sensors 284 provides a number of pedometer functions, including step counting, distance computations, and caloric consumption calculations. By entering the user's stride length and weight into memory, the microcontroller 282 can calculate and display, via the mobile terminal's display, various statistics of interest, including total distance traveled, total calories burned, speed, elapsed time, and steps per minute.

A heart rate monitor can also be incorporated using an appropriate heart rate sensor coupled to the microcontroller 282. Various log functions can also be employed, by which the mobile terminal keeps records of the user's steps and/or distance on a per-walk and/or daily basis. The user, for example, can record daily distance or step totals in a particular log, and a number of different logs can be established to correspond to a number of different walking routes, for example.

In general, the acceleration sensor 284 can be implemented to detect user movement along the vertical axis (z-axis). When a person walks, there is z-axis movement of the body with each step. One approach to measuring distance walked by a person is to use this z-axis movement to determine how many steps have been taken, and then multiply the number of steps taken by the average stride length. The average stride length can, for example, be input to the microcontroller 282 via the user interface of the mobile terminal.

An algorithm for step counting that can be implemented by microcontroller 282 uses some manner of peak detection. Generally, sampling can be performed at a frequency of 10 to 20 Hz and then averaged down to 2 to 3 Hz to remove noise. The step detection routine then looks for a change in slope of the z-axis acceleration. These changes in slope indicate a step.

A more accurate approach to measuring distance walked by a person using step counting is to only look for the change in slope at appropriate times. Stride frequency tends to change no more than +/−15% per step during steady state walking. Detecting the peak of the acceleration sensor output signal only during a time window as predicted by the last few steps results in more accurate step counting.

Figure 3B:
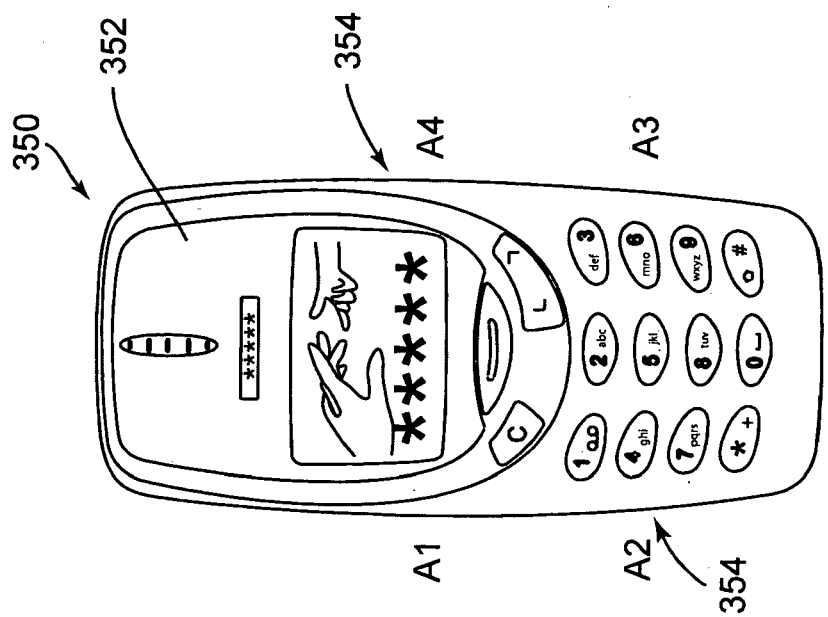
FIG. 3B shows a mobile terminal which incorporates body fat monitoring circuitry, including a number of probe electrodes provided on opposing sides of a mobile terminal, in accordance with an embodiment of the present invention.
Figure 3A:
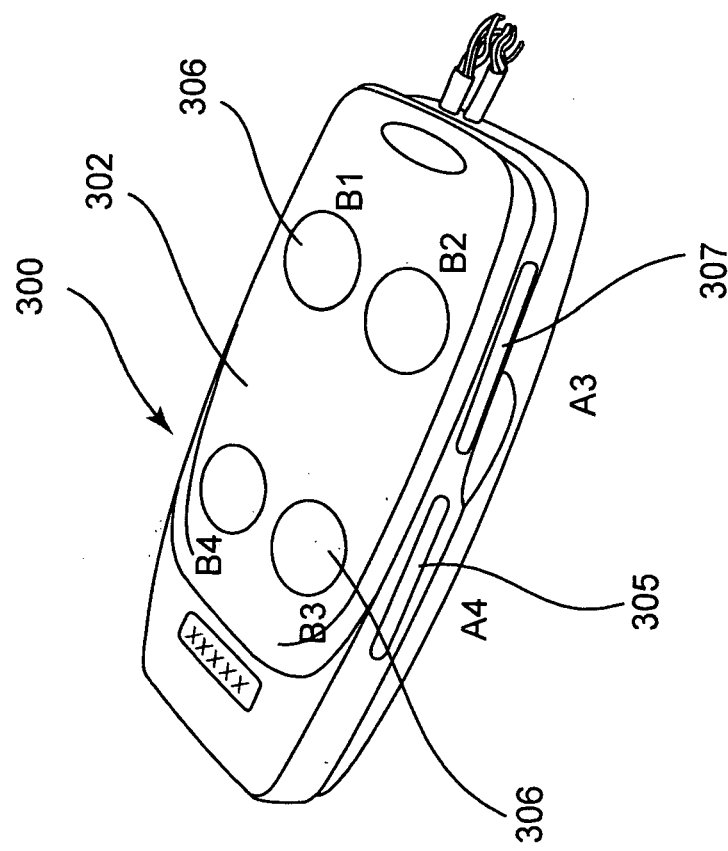
FIG. 3A shows a mobile terminal which incorporates body fat monitoring circuitry, including a number of electrodes provided on a cover and sides of a mobile terminal, in accordance with an embodiment of the present invention.

Turning now to FIG. 3A, there is shown a mobile terminal 300 which incorporates body fat monitoring circuitry, and which may include an acceleration sensor, in accordance with an embodiment of the present invention. According to this embodiment, a cover 302 of the mobile terminal 300 incorporates a number of electrodes 306. The electrodes 306 are shown mounted flush with the outer surface of the cover 302.

Depending on mobile terminal size and shape, the cover 302 may also include electrodes 307 mounted along one or more edges of the cover 302, as is also shown in FIG. 3A. It is understood that the electrodes 306/307 can alternatively be mounted on the housing 305 of the mobile terminal 300 or on both the housing 305 and the cover 302.

The cover 302 includes electrical contacts (not shown) that connect with corresponding electrical contacts on the housing 305 when the cover 302 is situated on the housing 305 for use in body fat monitoring. According to another configuration, the electrodes 305/307 can also be used as electrical connectors for connecting to equipment external to the mobile terminal.

It will be appreciated that a mobile terminal 300 may include electrodes mounted on the cover 302 only, to both the cover 302 and one or both sides of the housing 305, or to both the top of cover 302 and one or both sides of the cover 302. It is noted that the four cover electrodes 306 can alternatively be mounted to the back of the mobile terminal housing, in which case the functional cover need not be used.

In accordance with a four point probe technique employing a mobile terminal 300, the functional cover 302 includes four electrodes 306, shown as electrodes B1, B2, B3, and B4. In the embodiment shown in FIG. 3B, the mobile terminal 350 is shown without a cover and includes four electrodes 354 mounted on opposing sides of the mobile terminal's housing 352. In this embodiment, a functional cover that incorporates electrodes, such as that shown in FIG. 3A, is not employed. The four electrodes mounted on opposing sides of the housing in FIG. 3B are identified as electrodes A1, A2, A3, and A4.

Figure 4:
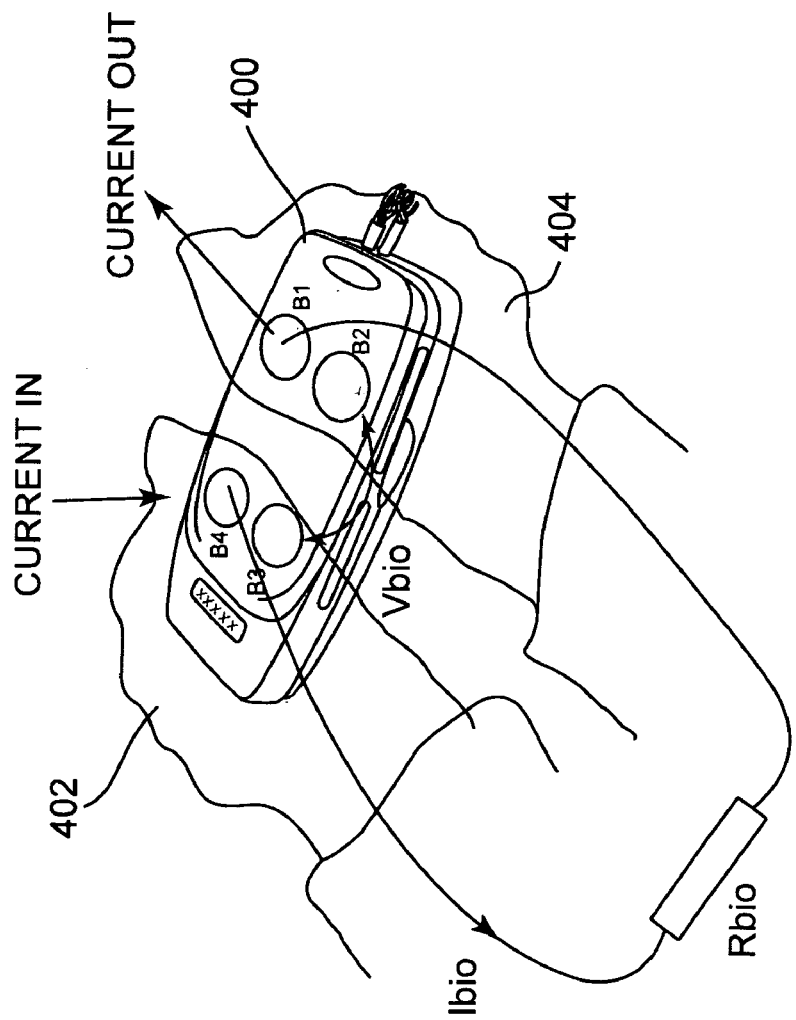
FIG. 4 illustrates a measurement configuration according to an embodiment of the present invention in which a body fat measurement is accomplished by injection and detection of monitoring signals communicated between electrodes disposed on a cover of a mobile terminal and a user's body via the user's hands.

The location of electrodes B1–B4 and A1–A4 on the mobile terminal cover and/or housing is important for purposes of understanding the various body fat measuring techniques described below and in connection with FIGS. 4–6. FIG. 4 illustrates one particular four point probe method that utilizes four electrodes, B1–B4, mounted on a functional cover 400 of a mobile terminal. FIG. 4 illustrates a user grasping the mobile terminal such that electrodes B3 and B4 contact the palm of the user's left hand 402 and electrodes B2 and B1 contact the palm of the user's right hand 404. Although shown in FIG. 4, the side mounted electrodes are not needed for performing the instant body fat measuring technique depicted in FIG. 4.

According to this measuring technique, a monitoring signal source vector employs electrodes B4 and B1, and a monitoring signal detection vector employs electrodes B3 and B2. A monitoring signal, preferably in the form of an AC drive current, is injected into the user's left palm via the B4 electrode, propagates through the body, and returns to the mobile terminal cover 400 via the B1 electrode. The B4 electrode, body, and B1 electrode thus define the $I_{bio}$ source current path for this measuring method. The values of $V_{bio}$, developed between the B3 and B2 electrodes, $I_{bio}$, and $R_{bio}$ can be computed using Equation [1] above.

Figure 5:
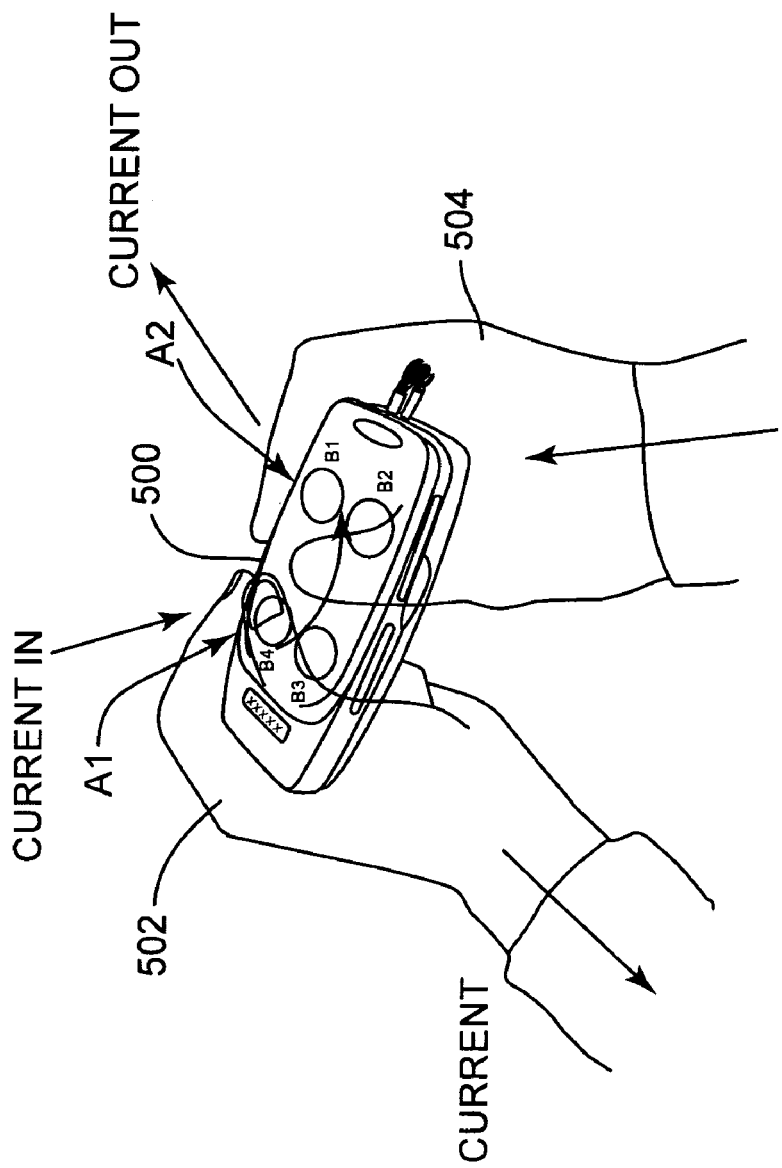
FIG. 5 illustrates a measurement configuration according to a further embodiment of the present invention in which a body fat measurement is accomplished by injection and detection of monitoring signals communicated between electrodes disposed on a cover and sides of a mobile terminal and a user's body via the user's fingers and thumbs.

FIG. 5 illustrates a four point probe technique employing a mobile terminal in accordance with another embodiment of the present invention. According to this embodiment, two cover electrodes, B4 and B1, and two side electrodes, A1 and A2, are employed. The two side electrodes, A1 and A2, are preferably mounted to an edge of the cover 500 of the mobile terminal, but may alternatively be mounted to the side of the mobile terminal's housing. As is shown in FIG. 5, a user grasps the mobile terminal such that the user's index finger of the left hand 502 contacts electrode A1, and the user's index finger of the right hand 504 contacts electrode A2. The mobile terminal is grasped such that the user's left thumb contacts electrode B4, and the user's right thumb contacts electrode B1.

According to this measuring technique, a monitoring signal source vector employs electrodes A1 and A2, and a monitoring signal detection vector employs electrodes B4 and B1. A monitoring signal, $I_{bio}$, is injected into the user's left thumb via the A1 electrode, propagates through the body, and returns to the mobile terminal cover 500 via the A2 electrode. The values of $V_{bio}$, developed between the B4 and B1 electrodes, $I_{bio}$, and $R_{bio}$ can be computed using Equation [1] above.

Figure 6:
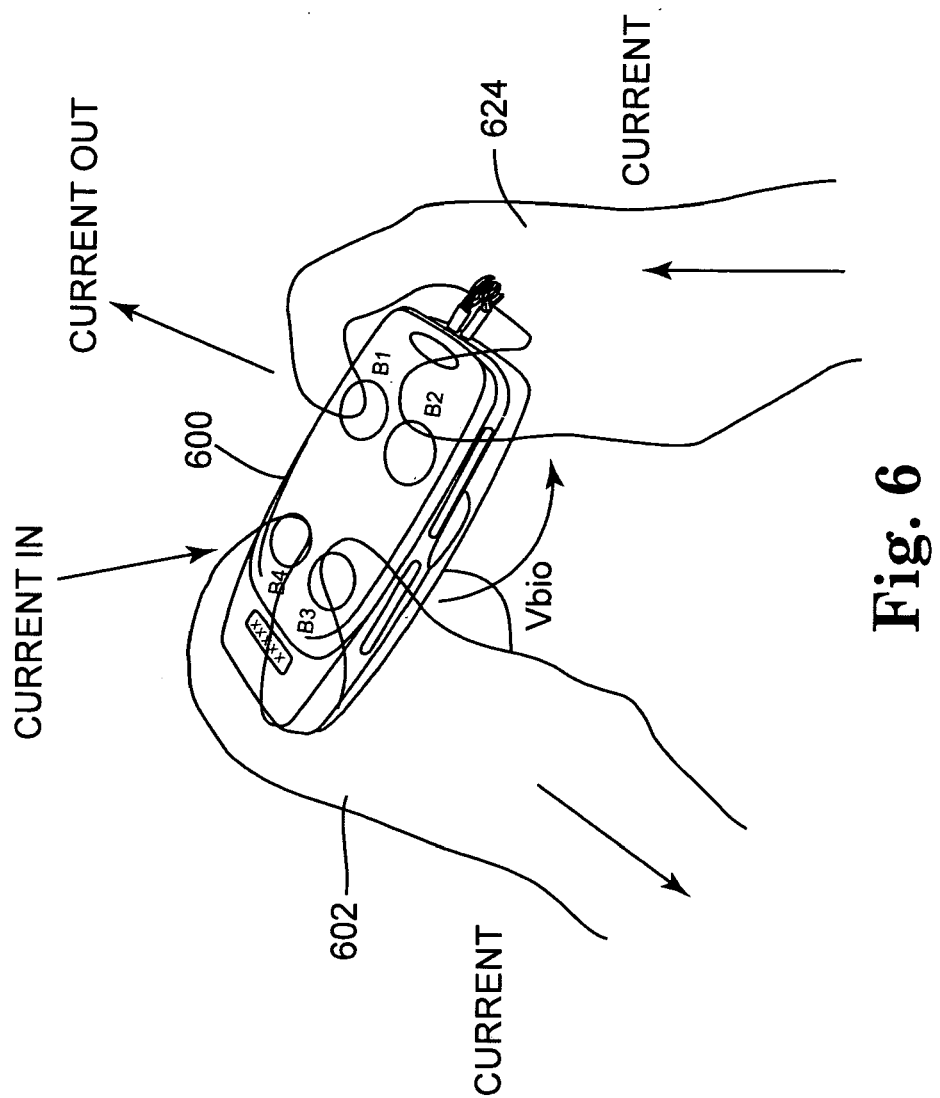
FIG. 6 illustrates a measurement configuration according to another embodiment of the present invention in which a body fat measurement is accomplished by injection and detection of monitoring signals communicated between electrodes disposed on a cover of a mobile terminal and a user's body via the user's fingers and thumbs.

FIG. 6 illustrates a four point probe technique employing a mobile terminal in accordance with yet another embodiment of the present invention. According to this embodiment, four cover electrodes, B1–B4, are employed. As is shown in FIG. 6, a user grasps the mobile terminal such that the user's index finger of the left hand 602 contacts electrode B4, and the user's index finger of the right hand 604 contacts electrode B1. The mobile terminal is grasped such that the user's left thumb contacts electrode B3, and the user's right thumb contacts electrode B2.

According to this measuring technique, a monitoring signal source vector employs electrodes B4 and B1, and a monitoring signal detection vector employs electrodes B3 and B2. A monitoring signal, $I_{bio}$, is injected into the user's left index finger via the B4 electrode, propagates through the body, and returns to the mobile terminal cover 600 via the B1 electrode. The values of $V_{bio}$, developed between the B3 and B2 electrodes, $I_{bio}$, and $R_{bio}$ can be computed using Equation [1] above.

Various other monitoring signal source and detection vectors can be employed. For example, a monitoring signal source vector can employ electrodes B4 and B1 in contact with left and right middle fingers, with a monitoring signal detection vector employing electrodes B3 and B2 in contact with the left and right index fingers. In accordance with another arrangement, a monitoring signal source vector can employ electrodes A4 and A3 in contact with left and right index fingers, with a monitoring signal detection vector employing electrodes A1 and A2 in contact with the left and right thumbs. It has been found that increasing the size of the side electrodes A1–A4 can improve measuring results. Those skilled in the art will appreciate that optimizing the monitoring signal source and detection vectors will be dependent on a number of factors, including housing/cover size and shape and electrode size and shape, among other factors.

In accordance with one approach for computing body fat percentage, the body fat monitoring circuitry of the present invention uses an equation that can be derived from a known formula referred to as Lukaski's and Bolonchuk's formula (see Lukaski & Bolonchuk, Aviation, Space and Environmental Medicine, 59, pp. 1163–1169 (1988)). According to this approach, total body water (TBW), which is a measure of all of the water in a user, both intracellular and extracellular, is computed as:

$$TBW = 0.372(S^2/R) + 3.05(\text{Sex}) + 0.142(W) - 0.069(\text{Age}) \quad [2]$$

where, S represents stature in centimeters, R represents bioresistance in ohms, W represents body weight in kilograms, Sex equals 1 for males, 0 for females, and Age represents the age of the user in years.

Using total body weight, the fat free mass (FFM) of the user, in kilograms, can be computed as:

$$FFM = \frac{TBW}{0.73} \quad [3]$$

Fat free mass (FFM) yields fat mass (FM), in kilograms, as follows:

$$FM = \text{Weight} - FFM \quad [4]$$

Percent body fat of the user can then be calculated using the following equation:

$$\% \text{ Fat} = \frac{FM}{\text{Weight}} \times 100 \quad [5]$$

An equation derived from Lukaski's and Bolonchuk's formula, as characterized in Equations [2] through [5] above, is of particular use when performing body fat measurements with body fat monitoring circuitry implemented with a mobile terminal. Because a mobile terminal is held by users in a particular way, there is additional resistance from the users' fingers. Equation [6] below is derived from Lukaski's and Bolonchuk's formula by linearizing the 1/R term and adding a term proportional to the stature of the user squared, as follows:

$$FP = A \cdot S^2 \cdot R \cdot \frac{1}{W} + B \cdot S^2 \cdot \frac{1}{W} + C \cdot N \cdot \frac{1}{W} + D \cdot \frac{1}{W} + E \cdot S^2 + F \quad [6]$$

where, FP represents fat percentage of the user, S represents stature in centimeters, R represents measured bioresistance in ohms, W represents weight of the user in kilograms, and N represents age of the user in years. It is noted that in Equation [6], N can range between 18 and 80.

The values of parameters A through F vary as a function of gender depending on various properties of measurement geometry. By way of non-limiting example, the following values of parameters A through F may be used for particular measurement geometries:

TABLE 1

| Parameter | Males | Females |
|---|---|---|
| A | $2.178 \times 10^{-4}$ | $1.185 \times 10^{-4}$ |
| B | −0.3710 | −0.3121 |
| C | 30.80 | 25.92 |
| D | 27.26 | 0.5282 |
| E | $6.565 \times 10^{-4}$ | $9.210 \times 10^{-4}$ |
| F | 64.20 | 70.09 |

It is noted that Equation 6 or one similar to Equation [6] or to Lukaski's and Bolonchuk's equation can be used to determine the fat percentage of persons younger than 18 years by suitable alteration of parameters A–F.

As was previously discussed, the inherent mobile communication capabilities of the mobile terminal device in combination with physiological conditions monitoring circuitry provide for enhanced functionality and user interaction with various health and diet related services available via a mobile network. For example, and with reference to FIG. 7, physiological conditions monitoring circuitry is supported by a portable cover 700, which is preferably a cover of a mobile terminal or other portable communications device, such as a cover that contacts an upper surface of the device. In another configuration, physiological conditions monitoring circuitry is supported by a housing of the mobile terminal or other portable communications device. In a further configuration, physiological conditions monitoring circuitry is supported by each of a housing and a cover of the mobile terminal or other portable communications device.

In accordance with a further embodiment of the present invention, a variety of portable covers are changeably useable with a mobile terminal device (e.g., cellular phone). Each cover can incorporate electronic circuitry and, if applicable, sensors for providing various functionality. For example, a particular cover can incorporate body fat monitoring circuitry as described above. Various sports and gaming related covers, for example, can incorporate circuitry and functionality that facilitates enhanced user interaction with a mobile terminal device and network services.

Figure 7:
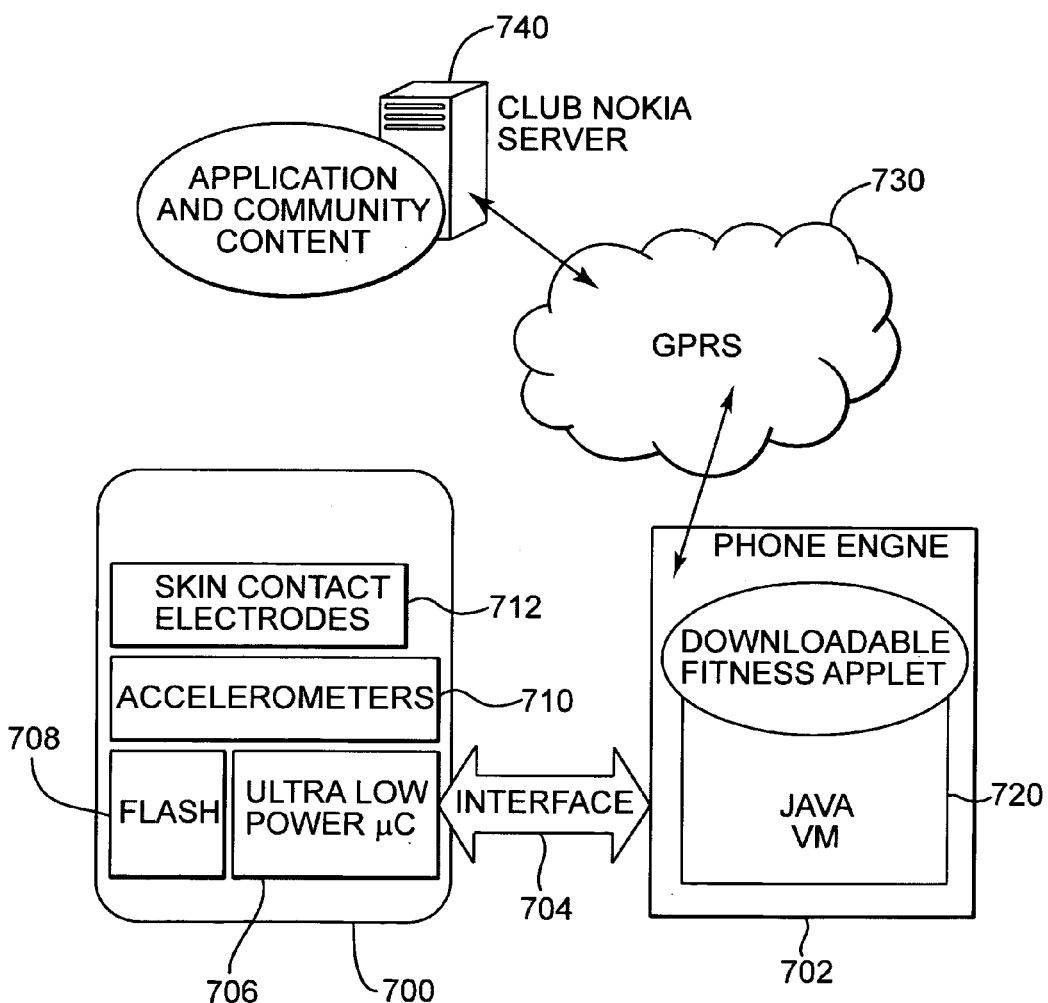
FIG. 7 illustrates a system for facilitating user access to, and interaction with, a variety of network services via a mobile terminal device incorporating or otherwise communicatively coupled to physiological conditions monitoring circuitry according to an embodiment of the present invention.

According to one illustrative configuration of the system depicted in FIG. 7, for example, a sports related cover 700 incorporates a number of skin contact electrodes 712 and one or more accelerometers 710 that provide for various physiological conditions monitoring (e.g., body fat, heart rate, blood pressure) and various pedometer functions as previously discussed. The cover 700 further incorporates a microprocessor 706, such as an ultra low power consumption microprocessor. A flash memory 708 or other non-volatile memory is coupled to the microprocessor 706. An interface (not shown) couples the mircoprocessor 700 with the electrodes 712 and accelerometers 710.

A device interface 704 communicatively couples the microprocessor 706 of the cover 700 with the mobile terminal, which is shown to include a phone engine 702. The phone engine 702 can be implemented to support a Java virtual machine (VM) 720, which can receive various types of Applets from a server 740 via a network 730. For example, the server 740 can download information in the form of various fitness, health, diet, and cooking Applets to the phone engine 702 of the mobile terminal device via the network 730.

The server 740 can support a wide variety of user services. For example, the server 740 can support applications and content for facilitating user access to, and interaction with, different virtual communities associated with each of the available services. A user, for example, can compare his or her diet with other members of a given community. Tips and experience with weight loss can be shared as between the user and members of a given community. Questions and answers can be exchanged with a personal trainer or diet expert on a group or individual basis. Exercise routines, effectiveness information, and activity level information can similarly be shared as between the user and members of a given community. Different services can thus be established to provide for user interaction with various target groups of users.

The foregoing description of the various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A mobile terminal device, comprising:
   a housing supporting a display;
   a cover detachably coupled to the housing;
   a processor;
   a user interface for facilitating user interaction with the mobile terminal device, the cover configured to cover at least a portion of the display and the user interface when coupled to the housing; and
   body fat monitoring circuitry comprising a tactile interface, at least the tactile interface supported by the housing cover, the monitoring circuitry communicating monitoring signals to a portion of a user's body via the tactile interface, the processor computing a parameter associated with the user's body fat in response to the communication of the monitoring signals.

2. The device of claim 1, wherein the processor computes a resistance to the communication of the monitoring signals and computes the user's body fat parameter using the computed resistance.

3. The device of claim 1, wherein the body fat parameter comprises percent body fat.

4. The device of claim 1, wherein the body fat parameter comprises one or both of fat mass and total body water.

5. The device of claim 1, wherein the tactile interface comprises a plurality of electrodes supported by the housing cover.

6. The device of claim 1, wherein the tactile interface comprises a plurality of electrodes supported by a common surface of the housing cover.

7. The device of claim 1, wherein the tactile interface comprises a plurality of electrodes supported by two or more surfaces of the housing cover.

8. The device of claim 1, wherein the monitoring signals produced by the monitoring circuitry comprise sinusoidal current or voltage signals.

9. The device of claim 1, wherein the monitoring signals produced by the monitoring circuitry comprise square wave current or voltage signals.

10. The device of claim 1, wherein the monitoring signals produced by the monitoring circuitry comprise a current or voltage signal having a frequency of about 50 kHz or greater.

11. The device of claim 1, wherein the monitoring signals produced by the monitoring circuitry comprise a current signal having an amperage less than about 1 mA.

12. The device of claim 1, wherein the monitoring circuitry maintains the monitoring signals at a substantially constant amperage or voltage.

13. The device of claim 1, wherein the user interface facilitates input of user information, the user information comprising one or more of gender, body weight, age, and height of the user, the processor using the user information to compute the parameter associated with the user's body fat.

14. The device of claim 1, wherein the tactile interface comprises a plurality of electrodes for communicating the monitoring signals to and from the portion of the user's body, and one or both of the housing and housing cover comprises an interface configured for communicating electrical signals between the processor and a device external to the mobile terminal device.

15. The device of claim 1, wherein the mobile terminal device comprises circuitry for communicating with a network and accessing one or more network services associated with user fitness or health.

16. A mobile terminal device, comprising:
a housing supporting a display;
a cover detachably coupled to the housing;
a user interface for facilitating user interaction with the mobile terminal device, the cover configured to cover at least a portion of the display and the user interface when coupled to the housing;
an acceleration sensor;
body fat monitoring circuitry comprising a tactile interface, at least the tactile interface supported by the housing cover, the monitoring circuitry communicating monitoring signals to a portion of a user's body via the tactile interface; and
a processor, the processor computing a parameter associated with the user's body fat in response to the communication of the monitoring signals and using an acceleration signal produced by the acceleration sensor to compute a parameter associated with walking or running by the user.

17. The device of claim 16, wherein the acceleration signal comprises a counter signal indicative of a number of steps taken by the user.

18. The device of claim 16, wherein the parameter associated with walking or running by the user comprises a distance traveled by the user.

19. The device of claim 16, wherein the parameter associated with walking or running by the user comprises calories consumed by the user during walking or running.

20. The device of claim 16, wherein the parameter associated with walking or running by the user comprises average speed or average steps per minute.

21. The device of claim 16, wherein the user interface facilitates input of user information, the user information comprising one or more of gender, body weight, age, height, and stride length of the user, the processor using the user information to compute the respective parameters associated with the user's body fat and walking or running by the user.

22. The device of claim 16, wherein the processor computes a resistance to the communication of the monitoring signals and computes the user's body fat parameter using the computed resistance.

23. The device of claim 16, wherein the body fat parameter comprises percent body fat.

24. The device of claim 16, wherein the tactile interface comprises a plurality of electrodes supported by the housing cover.

25. The device of claim 16, wherein the user interface comprises a keypad and further comprises a plurality of electrodes integrated into one or more keys of the keypad.

26. The device of claim 16, wherein the tactile interface comprises a plurality of electrodes supported by a common surface of the housing cover.

27. The device of claim 16, wherein the tactile interface comprises a plurality of electrodes supported by two or more surfaces of the housing cover.

28. The device of claim 16, wherein the monitoring signals produced by the monitoring circuitry comprise sinusoidal or square wave current signals.

29. The device of claim 16, wherein the mobile terminal device comprises circuitry for communicating with a network and accessing one or more network services associated with user fitness or health.

30. A method of using a mobile terminal device comprising a detachable cover for facilitating wireless communication and body fat monitoring, comprising:
providing the mobile terminal device, the detachable cover, and body fat monitoring circuitry, the body fat monitoring circuitry comprising a plurality of electrodes, the plurality of electrodes supported by the detachable cover for contacting portions of a user's hands, and wherein providing the detachable cover comprises covering at least a portion of a display and user interface with the detachable cover when coupled to the mobile terminal device;
transmitting monitoring signals between a first pair of the electrodes when in contact with the user's hands;
detecting, in response to transmission of the monitoring signals, a resistance between a second pair of the electrodes; and
computing a parameter associated with the user's body fat using the detected resistance.

31. The method of claim 30, further comprising receiving user information comprising one or more of gender, body weight, age, and height of the user, wherein computing the user's body fat parameter comprises using the user information to compute the parameter associated with the user's body fat.

32. The method of claim 30, wherein the first pair of electrodes are situated on the mobile terminal device to contact a distal portion of a palm of each of the user's hands, and the second pair of electrodes are situated on the mobile terminal device to contact a proximal portion of the palm of each of the user's hands.

33. The method of claim 30, wherein the first pair of electrodes are situated on the mobile terminal device to contact an index finger of each of the user's hands, and the second pair of electrodes are situated on the mobile terminal device to contact a thumb of each of the user's hands.

34. The method of claim 30, wherein the first pair of electrodes are situated on the mobile terminal device to contact a middle finger of each of the user's hands, and the second pair of electrodes are situated on the mobile terminal device to contact an index finger of each of the user's hands.

35. The method of claim 30, wherein the body fat parameter comprises percent body fat.

36. The method of claim 30, wherein the body fat parameter comprises percent body fat, and the method further comprises wirelessly communicating the percent body fat of the user to a remote data system and receiving a message concerning the user's percent body fat from the remote data system.

37. The method of claim 30, further comprising communicating with a network and accessing one or more mobile network services associated with user fitness or health.

38. The method of claim 30, further comprising communicating electrical signals between the mobile terminal device and a device external to the mobile terminal device.

39. The method of claim 30, wherein the mobile terminal device further comprises an acceleration sensor, the method further comprising computing a parameter associated with walking or running by the user using an acceleration signal produced by the acceleration sensor.

40. The method of claim 39, wherein the parameter associated with walking or running by the user comprises a distance traveled by the user.

41. The method of claim 39, wherein the parameter associated with walking or running by the user comprises calories consumed by the user during walking or running.

42. The method of claim 39, wherein the parameter associated with walking or running by the user comprises average speed or average steps per minute.

43. The method of claim 39, further comprising receiving user information, the user information comprising one or more of gender body weight, age, height, and stride length of the user, the method further comprising computing the respective parameters associated with the user's body fat and walking or running by the user using the user information.

44. The method of claim 39, wherein the body fat parameter comprises percent body fat, and the method further comprises wirelessly communicating the percent body fat of the user and the parameter associated with walking or running to a remote data system, and receiving a message concerning one or both of the user's percent body fat and a recommended walking or running regimen from the remote data system.

45. The method of claim 39, wherein the mobile terminal device is capable of over-the-air (OTA) communication with a network.

46. The method of claim 39, further comprising communicating with a mobile network and accessing one or more mobile network services associated with user fitness or health.

47. A portable cover configured for detachably coupling to a housing of a mobile communications device, and configured to cover at least a portion of the mobile communications device that includes a display and a user interface when coupled to the mobile communications device, the portable cover comprising:

a processor;

physiological conditions monitoring circuitry comprising a tactile interface supported by one or more surfaces of the cover, the monitoring circuitry communicating monitoring signals to a portion of a user's body via the tactile interface, the processor computing a parameter associated with a user's physiological conditions in response to communication of the monitoring signals; and an interface for coupling the processor with the monitoring circuitry.

48. The cover of claim 47, wherein the parameter computed by the processor is associated with the user's body fat.

49. The cover of claim 47, wherein the tactile interface comprises a plurality of electrodes.

50. The cover of claim 47, wherein the monitoring circuitry further comprises one or more accelerometers.

51. The cover of claim 47, further comprising a device interface configured to communicatively couple the processor of the portable cover to the mobile communications device.

* * * * *